United States Patent [19]

Nelson

[11] 4,305,291
[45] Dec. 15, 1981

[54] GAS ADSORPTION APPARATUS FOR DETERMINING THE GASEOUS SURFACE AREA OF A MATERIAL

[75] Inventor: Jordan R. Nelson, Trenton, N.J.

[73] Assignee: RCA Corporation, New York, N.Y.

[21] Appl. No.: 151,362

[22] Filed: May 19, 1980

[51] Int. Cl.³ .......................................... G01N 15/08
[52] U.S. Cl. ............................................... 73/432 PS
[58] Field of Search ............................. 73/432 PS, 38

[56] References Cited

U.S. PATENT DOCUMENTS

| | | | |
|---|---|---|---|
| 3,349,625 | 10/1967 | Benusa et al. | 73/432 PS |
| 3,464,273 | 9/1969 | Hendrix et al. | 73/432 PS |
| 3,500,675 | 3/1970 | Sandstede et al. | 73/432 PS X |
| 3,643,493 | 2/1972 | Vitovsky | 73/432 PS X |
| 3,732,736 | 5/1973 | Glaude et al. | 73/432 PS |
| 3,850,040 | 11/1974 | Orr, Jr. et al. | 73/432 PS |

OTHER PUBLICATIONS

Cahen et al., *Surface Area Determination by the Continuous Flow Method*, In Anal. Chem. 34(2):pp. 259–260 Feb. 1963.
Daeschner et al., *An Efficient Dynamic Method for Surface Area Determinations*, In Anal. Chem. 34(9):pp. 1150–1155 Aug. 1962.
ANSI/ASTM D 3037–78, *Carbon Black-Surface Area by Nitrogen Adsorption*, pp. 627–643.
Williams, C. J., *Gravimetric Adsorption*, In American Laboratory, pp. 1163–1169, Jun. 1969.
Mahajan et al., *Analytical Methods for Coal & Coal Prod.* vol. I, Pa. Chapter 4, pp. 125–161, 1978.
Allen, T., *Particle Size Measurement*, London, Chapman & Hall, 1968, Chapter 16, pp. 355–393.
*Micrometrics Surface Area Analyzers*, In Micrometrics publication, Norcross, Ga.

*Primary Examiner*—Charles A. Ruehl
*Assistant Examiner*—Joseph W. Roskos
*Attorney, Agent, or Firm*—Birgit E. Morris; Allen Bloom

[57] ABSTRACT

An apparatus for determining the gaseous surface area of a material. The apparatus incorporates, inter alia, a novel manifold structure that permits the testing of multiple samples of the material in quick succession.

6 Claims, 1 Drawing Figure

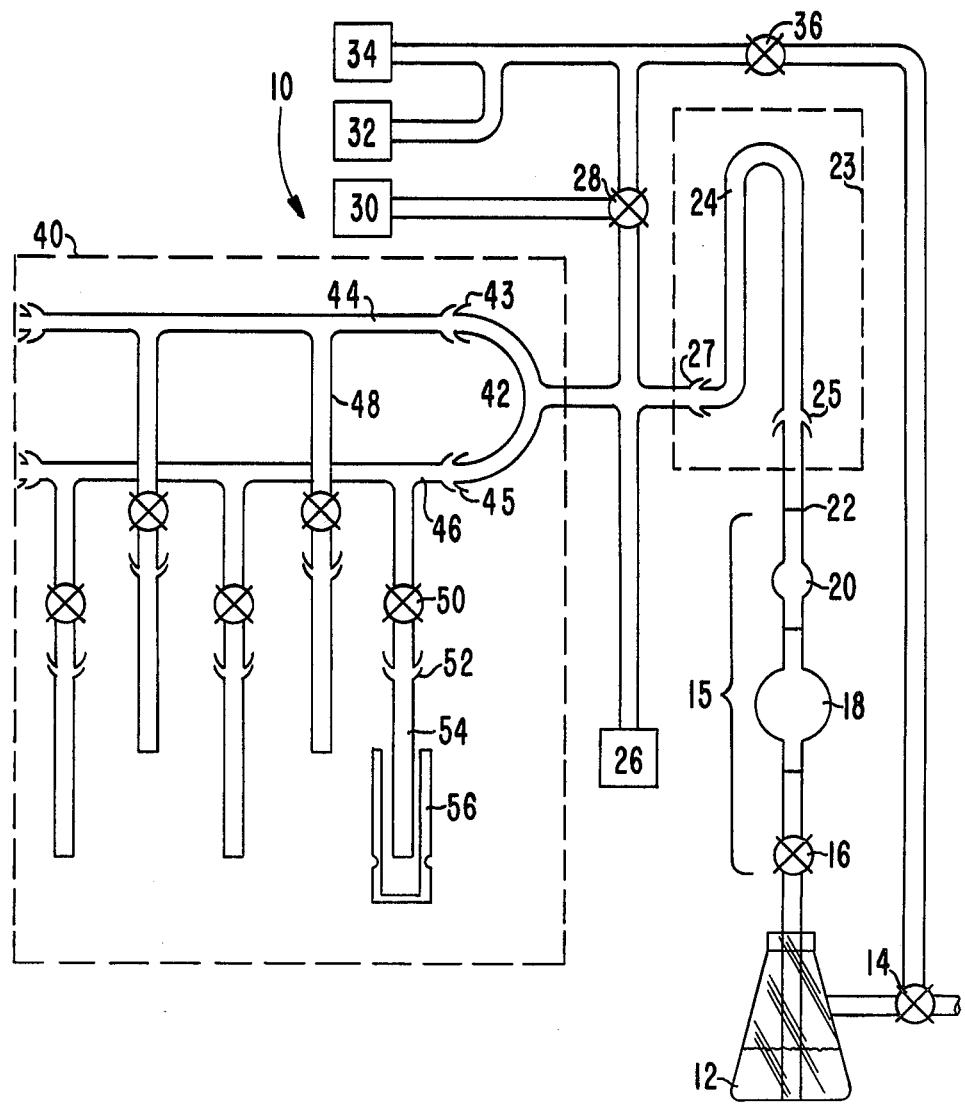

GAS ADSORPTION APPARATUS FOR DETERMINING THE GASEOUS SURFACE AREA OF A MATERIAL

This invention relates to an improved apparatus for determining the surface area of solid particles and a method of screening same. More specifically, this invention relates to an improved apparatus for determining the surface area of carbon black particles.

BACKGROUND OF THE INVENTION

One of the parameters used to quantify the quality of particles such as carbon black is the surface area, as measured with respect to a gas such as nitrogen. Another parameter used to quantify the quality of the carbon black is the pore size distribution of the carbon black.

The surface area of a solid material has been determined in the past in an apparatus which operates in accordance with the Brunauer-Emmett-Teller (BET) equation given below:

$$\frac{P}{V(P_o - P)} = \frac{1}{V_m C} + \frac{(C-1)}{V_m C} \cdot \frac{P}{P_o}$$

where;

V is the volume adsorbed at equilibrium pressure P, $P_o$ is the saturation pressure of the adsorbate at the adsorption temperature, $V_m$ represents the monolayer capacity, and $C = \exp[(E_1 - E_L)/RT]$ where $E_1$ is the heat of adsorption of the first monolayer of adsorbate and $E_L$ is the heat of liquefaction of the adsorbate.

The pore size distribution can be calculated, inter alia, by either mercury porosimetry or the capillary condensation of nitrogen. Mercury porosimetry is usually limited to materials which have pore diameters in excess of 7.0 nanometers. Carbon blacks normally have a significant amount of porosity in pores which are less than 7.0 nanometers in diameter. To determine the pore size distribution of a carbon black, capillary condensation of nitrogen is a more suitable method and it can determine pore size distributions in the diameter range of from 2.0 to 30 nanometers using a method devised by Cranston and Inkley. The Cranston and Inkley method for estimating the pore size distribution of a material requires the determination of a isotherm or several isotherms at different temperatures. For example, a suitable isotherm should be the ratio of the saturation pressure of nitrogen at one atmosphere pressure and 77° K. ($P_o$) to the equilibrium adsorption pressure of nitrogen in torr ($P_i$) less than $P_o$. The variables are moles of gas and pressure. The $P_i/P_o$ ratio should be measured for values from zero to one. With a determination of the isotherm, the pore size distribution can be estimated by the formula of Cranston and Inkley given below:

$$v_r \delta r = \frac{(r - t_r)^2}{r^2} V_r \delta r + \delta t \int_{r + \delta r}^{\infty} \frac{(r - t_r)}{r} \frac{2V_r}{r} dr$$

where $v_r \delta r$ is the total volume of nitrogen adsorbed (as liquid) and $V_r \delta r$ is the total volume of pores in the range $\delta r$ considered.

Heretofore, an apparatus which could measure the pore size distribution or the surface area of a carbon black with respect to a given gas such as nitrogen as either extremely cumbersome or limited in the number of determinations that could be made at a given time. Thus, a compact apparatus for screening multiple samples of solid particles such as carbon black would be highly desirable.

BRIEF DESCRIPTION OF THE DRAWING

FIG. 1 illustrates an apparatus for determining the pore size distribution and surface volume of a solid material.

DETAILED DESCRIPTION OF THE INVENTION

The invention will be illustrated by referring to the gas adsorption apparatus 10 in FIG. 1. Apparatus 10 has a fluid reservoir 12 such as a mercury reservoir for adjusting and determining the volume of the apparatus 10. The reservoir 12 vents to the atmosphere or to a positive or negative pressure source through valve 14 and to the volume adjusting and calibrating section 15 of the apparatus 10 through valve 16.

The volume of the apparatus can be adjusted and determined by section 15. Section 15 includes the calibrated bulbs 18 and 20 and a capillary restriction 22. The capillary restriction 22 also maintains the rate of flow of mercury within safe limits during the operation of the apparatus.

The apparatus 10 incorporates a fluid constriction section 23 such as mercury safety loop 24 connected into the apparatus 10 by joints 25 and 27. The fluid constriction section 23 is of a sufficient height and design to prevent mercury from contaminating the sampling section 40 of the apparatus 10 during operation at subatmospheric pressure. The safety loop 24 project upward from the plane formed by the U-shaped manifold in section 40 of the apparatus. In addition, the use of a mercury safety loop 24 enables the construction of an apparatus 10 which is more compact than an apparatus 10 without the mercury safety loop 24.

Attached to the mercury safety loop 24 beyond the joint 27 is a pressure gauge 26 such as an electronic pressure gauge, a Baraton pressure gauge, or for example, a mechanical pressure gauge such as a mercury nanometer. A valve 28 connects to an inert gas source 30 such as nitrogen, carbon dioxide, helium, and the like. The valve 28 also connects to a vacuum pump 34, such as a diffusion pump, and a thermocouple gauge 32. The vacuum pump 34 can also be connected to the mercury reservoir 12 through valve 36.

The sampling section 40 of the apparatus 10 includes a U-shaped manifold comprising a base member 42 connected to conduit legs 44 and 46 through joints 43 and 45. The conduit legs 44 and 46 and base member 42 form a first plane. Transverse to the first plane, a plurality of conduits 48 are connected to the conduit legs 44 and 46. The conduits 48 are preferably attached along the conduit legs 44 and 46 in alternating sequence. The conduits are further arranged such that an operator can reach between two conduits attached to one conduit leg to a conduit attached to the other conduit leg. The conduit legs 44 and 46 are fabricated in alternating sections having three and two conduits attached thereto. Of course, the conduit legs can be fabricated in sections with more conduits or fewer conduits attached thereto. The fabrication of the conduit legs in sections permits the rapid expansion of the sampling section or quick replacement of broken sections. The sampling section can quickly be expanded to seven or more conduits and preferably about 10 through the addition of more conduit legs.

Attached to each conduit 48 through a valve 50 and joint 52 is a sampling tube 54. The valve 50 permits the sampling tube to be isolated from the rest of the apparatus. The temperature in the sample tube holder 54 can be varied by means of a heater or cooler illustrated as 56. For example, the heater can be a resistance heater and the cooler can be a dewar flask containing liquid nitrogen.

Prior to screening carbon black samples, the dead space volume of each of the sample tube holders 54 and the volume of the apparatus 10 is determined in accordance with standard procedures known in the art as outlined in *Analytical Methods for Coal and Coal Products* pp. 125-162 and specifically pp. 145-150, Academic Press, (1978), and *Particle Size Measurement*, pp. 372-375, Chapman and Hall, (1977), both of said articles incorporated herein by reference. The pore size distribution and surface area can be determined in accordance with ASTM D3037-78, incorporated herein by reference.

More specifically, the volume of the system is determined by pumping a positive pressure through valve 14 into flask 12 to force mercury up through the calibrated bulbs 18 and 20 to a hash mark on tube 22 and thereafter closing valve 14. A measured amount of a gas such as helium is introduced into the system through valve 28 and then the valve is closed. When the system reaches equilibrium, the change in pressure differential is measured by pressure gauge 26 and the volume of mercury in the bulb 20 is recorded. Thereafter, the valves 50 are opened sequentially so that the additional pressure drop can be used to determine the volume of the sample holders 54. With the volume of the apparatus and the volume of each of the sample holders 54 determined, the surface area and pore size distribution of the solid particle such as a carbon black sample can be determined as described below.

To determine the properties of the carbon black, a sample of from about 0.1 gram to about 4 grams of the carbon sample is placed in a sample holder 54 and stopped with glass wool to prevent the carbon from blowing out during evacuation of the apparatus. The weighing of a sample is the major source of error and therefore care should be taken during weighing. For high surface area carbons, an error of ±1 milligram translates into a ±5 m²/gm error in the final surface area determination. By changing the mercury level in the calibrated bulbs 18 and 20, the volume of the system, $V_{ad}$, is calculated according to the following formula:

$$V_{ad} = P_2 V_3 / (P_1 - P_2)$$

wherein $P_1$ and $P_2$ are the pressures before and after lowering mercury through the bulbs 18 and 20, and $V_3$ is the volume of bulbs 18 and 22. In practice $V_{ad}$ needs to be done only once using nitrogen unless the size of the system is changed. The volume of the sample tube, $V_{fs}$, is determined according to the following formula:

$$V_{fs} = V_{ad}(P_1 - P_2)/P_2$$

After flushing the gas line with nitrogen for 20 minutes, the nitrogen is added to the system, and the pressure ($P_{iad}$) is noted. The valve 50 to the sample holder 54 is then opened and the equilibrium pressure ($P_i$) is noted after 20 minutes. The valve 50 is then closed and more nitrogen added. The nitrogen adsorbed ($V_i$) for each addition of nitrogen can be calculated from the following equation.

$$V_i = \frac{T_o V_{ad}}{T_{RT} P_o W_s} (P_{iad} - P_i) - \frac{T_o V_{fs}}{T_{RT} P_o W_s} (P_i - P_{i-1})$$

where;

$T_o = 273.15°$ K.

$T_{RT} =$ room temperature, °K.

$P_o =$ saturation pressure of nitrogen, 760 torr at 77° K.

$P_{iad} =$ pressure of the nitrogen in the measuring system, torr $P_i =$ equilibrium adsorption pressure of the nitrogen, torr $V_{ad} =$ volume of the measuring system, cm³

$V_{fs} =$ volume of the sample holder, cm³ (e.g., 13 cm³)

$W_s =$ sample weight, gm

With the measurements of the drop in nitrogen pressure before and after introduction, the monolayer $V_m$ of nitrogen covering the carbon is calculated from the adsorption data using the Brunauer-Emmett-Teller equation.

The invention will be illustrated by the following examples, but it is to be understood that the invention is not meant to be limited to the details described therein.

EXAMPLES 1-10

About 0.2000 gram samples of a carbon black, Ketjenblack EC, a product of the Akzo Chemie Company (Belgium), were weighed and placed into clean dried sample holders. The volume of the apparatus excluding the sample holders and bulbs was 26.72 cm³, volume of the sample holders varied from 11.50 cm³ to 13.70 cm³, and the volume of the calibration bulbs were 9.510 cm³ and 28.050 cm³.

Residual moisture in the carbon black can be estimated at about 1%, but pre-drying of the samples would decrease weighing errors. About 2 inches of glass wool was placed into the sample holder. Thereafter, the male side of the joint was greased and attached to the rest of the apparatus. After all the tubes were connected, the samples were heated to about 120° C. and dried overnight. After drying, the valves to the sample holders were closed. The sample holders were placed in liquid nitrogen for about 20 minutes. Thereafter, one atmosphere of nitrogen was admitted into the apparatus and the nitrogen was permitted to reach equilibrium. The $P_{iad}$, the $V_{ad}$, the temperature, and the sample number were recorded. Thereafter, the sample valve was opened and after 20 minutes the $P_i$ was recorded. Additional nitrogen was introduced into the apparatus in accordance with the previously outlined procedure until the $P_i$ is greater than 30 torr but less than 50 torr. The procedure was repeated for each sample holder. The table below gives the weight of the sample and nitrogen surface area.

TABLE I

| Example | Carbon Black | Wt. of Sample (gm) | Surface Area (m²/gr) |
|---|---|---|---|
| 1 | Batch 1 | .1964 | 882.56 |
| 2 | Batch 2 | .2000 | 902.61 |
| 3 | Batch 3 | .2073 | 930.75 |
| 4 | Batch 4 | .1966 | 874.94 |
| 5 | Batch 5 | .1962 | 887.68 |
| 6 | Batch 6 | .1970 | 971.57 |
| 7 | Batch 7 | .2060 | 889.93 |
| 8 | Batch 8 | .1850 | 895.73 |
| 9 | Batch 9 | .2020 | 905.32 |

TABLE I-continued

| Example | Carbon Black | Wt. of Sample (gm) | Surface Area ($m^2/gr$) |
| --- | --- | --- | --- |
| 10 | Batch 10 | .1935 | 898.89 |

What is claimed is:

1. In an apparatus for determining the surface area of a solid material which comprises fluid means for adjusting the volume of the apparatus, means for changing the pressure in the apparatus, a gas source for introducing a known volume of gas into said apparatus, means for recording the pressure of the apparatus before and after the introduction of said known volume of gas into said apparatus, and means for varying the temperature in a sample holder, the improvement comprising, a U-shaped manifold, said manifold having a base member connected to said apparatus and two substantially parallel conduit legs joined to said base conduit member, said base conduit member and said conduit legs defining a first plane, a plurality of conduits connecting a plurality of sample holders to the conduit legs, said conduits and said sample holders lying in planes which are transverse to said first plane wherein the conduits connected along one of said conduit legs are disposed substantially parallel to and off-centered from the conduits connected along the opposite leg.

2. An apparatus according to claim 1 wherein the conduits connected to one of said conduit legs are substantially centered between the conduits connected to the opposite conduit leg.

3. An apparatus according to claim 2 wherein said conduit legs are fabricated in sections having conduits attached thereto.

4. An apparatus according to claim 1 further incorporating a fluid constriction means to preclude said fluid from contaminating the material in said sample holder.

5. An apparatus according to claim 4 wherein the constriction is an inverted U-shaped member projecting above the plane of the U-shaped manifold.

6. An apparatus according to claim 5 wherein said fluid is mercury.

* * * * *